United States Patent [19]

Umetsu et al.

[11] Patent Number: 5,051,238

[45] Date of Patent: Sep. 24, 1991

[54] AUTOMATIC ANALYZING SYSTEM

[75] Inventors: Hiroshi Umetsu, Katsuta; Hiroshi Hashimoto, Ibaraki; Kyoko Imai, Katsuta; Hajime Betsui, Katsuta; Tadashi Ohishi, Katsuta, all of Japan

[73] Assignee: Hitachi, Ltd., Tokyo, Japan

[21] Appl. No.: 272,345

[22] Filed: Nov. 17, 1988

[30] Foreign Application Priority Data

Nov. 20, 1987 [JP] Japan .................. 62-293400
Aug. 26, 1988 [JP] Japan .................. 63-210748

[51] Int. Cl.⁵ .................................. G01N 35/06
[52] U.S. Cl. ............................. 422/64; 422/67
[58] Field of Search ....................... 422/63–67; 277/53, 57

[56] References Cited

U.S. PATENT DOCUMENTS

| 2,946,609 | 7/1960 | Comery | 277/53 |
|---|---|---|---|
| 4,234,538 | 11/1980 | Ginsberg et al. | 422/64 |
| 4,774,055 | 9/1988 | Wakatake | 422/64 |
| 4,778,763 | 10/1988 | Makiguchi et al. | 422/64 |
| 4,849,177 | 7/1989 | Jordan | 422/64 |
| 4,871,683 | 10/1989 | Harris et al. | 422/64 |
| 4,906,433 | 3/1990 | Minekane | 422/64 |
| 4,908,320 | 3/1990 | Zakowski et al. | 422/64 |
| 4,933,147 | 6/1990 | Hollar et al. | 422/64 |

FOREIGN PATENT DOCUMENTS

| 0041378 | 12/1981 | European Pat. Off. . |
|---|---|---|
| 0052006 | 5/1982 | European Pat. Off. . |
| 0074102 | 3/1983 | European Pat. Off. . |
| 2025678 | 2/1974 | Fed. Rep. of Germany . |
| 3015051 | 10/1980 | Fed. Rep. of Germany . |
| 3102774 | 12/1981 | Fed. Rep. of Germany . |
| 3318573 | 1/1984 | Fed. Rep. of Germany . |
| 3838361 | 5/1989 | Fed. Rep. of Germany . |
| 50-70085 | 6/1975 | Japan . |
| 62-217163 | 9/1987 | Japan . |

Primary Examiner—Peter Kratz
Attorney, Agent, or Firm—Fay, Sharpe, Beall, Fagan, Minnich & McKee

[57] ABSTRACT

An automatic analyzing system has a sample table for supporting a plurality of sample vessels and a reagent table for supporting a plurality of reagent vessels. The sample table and the reagent table are fixed to a common drive shaft. The system further has a rotatable reaction table for supporting a plurality of reaction vessels. The reaction table is arranged in a side-by-side relation to the sample table and the reagent table. The system further has a single pipetting device disposed between the reaction table and the stack of the sample table and the reagent table for a swinging motion therebetween so as to suck samples and reagents from the sample vessels and the reagent vessels and to deliver the same to the reaction vessels. The pipetting device is operated in such a manner as to transfer all the samples to the reaction vessels followed by the supply of the reagents to these reaction vessels.

3 Claims, 11 Drawing Sheets

AUTOMATIC ANALYZING SYSTEM

BACKGROUND OF THE INVENTION

1. Field of the Invention

The present invention relates to an automatic analyzing system and also to an analyzing method which makes use of this system. More particularly, the present invention is concerned with an automatic analyzing system and method in which, though not exclusively, a plurality of kinds of reagents corresponding to a plurality of measurement items are prepared on a reagent table and are successively supplied into reaction vessels on a reaction table so as to cause reactions between samples and the respective reagents thereby automatically analyzing the samples.

2. Description of the Prior Art

An analyzing system of the above-mentioned type is disclosed in Japanese Unexamined Patent Publication No. 50-70085. This system includes reaction, sample and reagent disks all arranged separately from each other. The system also has a plurality of reaction vessels arranged on the reaction disk and corresponding to different measurement items. In operation, the samples and the reagents are supplied to the reaction vessels by means of pipetting mechanisms which are prepared independently for the samples and the reagents. Namely, a pipetting mechanism is used exclusively for the transfer of the samples, and another pipetting mechanism is used exclusively for the reagents. In order to increase the number of the items to be checked, this known system employs an independent pipetting mechanism for the single reagent disk. When two types of reagents, e.g., a first reagent and a second reagent, are dispensed on a single reagent disk, the reagent disk needs two pipetting systems. In consequence, the arrangement is complicated and the cost of production of the system is raised correspondingly. In addition, the analyzing operation with this system is very laborious and time-consuming.

Japanese Unexamined Patent Publication No. 62-217163 discloses another automatic analyzing system. This automatic analyzer has a sample table having sample vessels and a reaction table coaxial with the sample table. The system also has first and second reagent tables which are disposed on different axes spaced from the common axis of the sample table and the reaction table. In consequence, this system requires that the sampling pipette devices operate independently for the samples, i.e. the first reagent and second reagent, with the results that the system becomes complicated in construction and large in size and that the production cost is raised correspondingly. In addition, the analyzing operation is time-consuming as in the case of the system disclosed in Japanese Unexamined Patent Publication No. 50-50085.

SUMMARY OF THE INVENTION

Accordingly, an object of the present invention is to provide an automatic analyzing system having an extremely simplified construction, as well as a method which enables an easy analytical measurement particularly when a plurality of measurement items are employed, thereby overcoming the above-described problems of the prior art.

Another object of the present invention is to provide an analyzing system and an analyzing method in which analytical measurement of a plurality of measurement items can be conducted by a single pipetting mechanism.

To this end, according to one aspect of the present invention, there is provided an automatic analyzing system comprising: a rotatable sample table for supporting a plurality of sample vessels; a rotatable reagent table arranged coaxially with the sample table and designed to support a plurality of reagent vessels; a rotatable reaction table arranged in a side-by-side relation to the sample table and the reagent table and carrying a plurality of reaction vessels; and a single pipetting device movable over the sample table, the reagent table and the reaction table so as to remove samples and reagents from selected sample vessels and selected reagent vessels on the sample table and the reagent table and to deliver the thus removed samples and reagents to selected reaction vessels on the reaction table.

According to another aspect of the invention, there is provided an automatic analyzing method which makes use of the automatic analyzing system having the construction stated above, comprising: a sample pipetting step in which a predetermined quantity of sample is transferred from one of the sample vessels on the sample table to a predetermined one of the reaction vessel by means of the pipetting device; subsequent sample pipetting steps in which the sample table and the reaction table are intermittently rotated so as to transfer predetermined amount of the sample from each of the successive sample vessels to each of the successive reaction vessels by means of the pipetting device; a washing step conducted between each adjacent pair of successive sample pipetting steps for washing the pipetting device; reagent pipetting steps in which predetermined quantities of reagent are transferred from successive reagent vessels on the reagent table to successive reaction vessels by means of the pipetting device; and a further washing step conducted between each adjacent pair of reagent pipetting steps.

The automatic analyzing system of the present invention has a construction which is remarkably simplified as compared with known systems, because analytical measurement of a plurality of measuring items can be executed by a single pipetting device. The production cost can be reduced accordingly.

The analyzing method of the invention remarkably facilitates the analyzing operation. Namely, even if a multiplicity of, e.g., 5, reagents have to be used for a multiplicity single analytical measurement item, the measurement can be executed with a single pipetting mechanism so that the analysis can conveniently be executed in quite a simple manner.

The above and other objects, features and advantages of the present invention will become clear from the following description.

DESCRIPTION OF THE PREFERRED EMBODIMENTS

Figure 1:
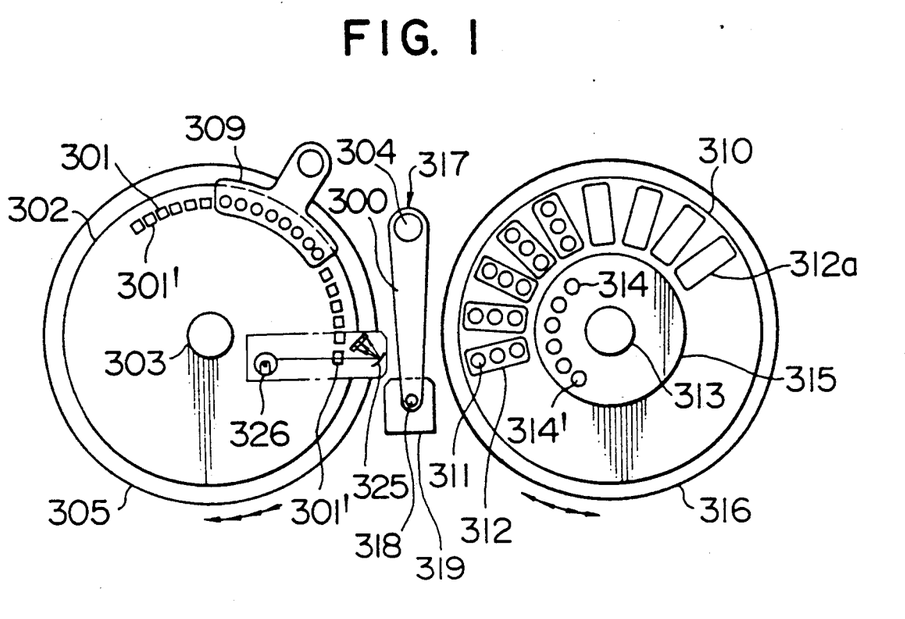
FIG. 1 is a plan view of an embodiment of an automatic analyzing system in accordance with the present invention, in which the system is illustrated schematically for facilitating understanding of the basic idea of the present invention.

Referring to FIG. 1, a first embodiment of the analyzing system in accordance with the present invention has a shaft 313 which carries a sample table 315 having a plurality of sample vessel pockets 314 which are arranged at a predetermined pitch or interval in the circumferential direction. The sample table 315 is rotatable with the shaft 313 about the axis of the shaft 313. A reagent table 310 having a diameter greater than that of the sample table 315 is fixed to a portion of the shaft 313 which is axially spaced downward from the sample table 315. The reagent table 310 is also rotatable with the shaft 313 about the axis of the shaft 313. The reagent table 310 supports a plurality of reagent vessels 311. In the embodiment shown in FIG. 1, the reagent table 310 has a plurality of reagent pack pockets 312a which are arranged radially around the shaft 313. Each of these reagent pack pockets 312a receives a reagent pack 312 which includes three reagent vessels 311 charged with different reagents. Thus, a plurality of reagent packs 312 are arranged on the reagent table 310 radially around the shaft 313. The system further has a reaction table 302 which is fixed to a shaft 303 such that the reaction table 310 is set in a side-by-side relation to the sample table 315 and the reagent table 310 on the shaft 313. The reaction table 302 is rotatable with the shaft 303 about the axis of this shaft. The reaction table 302 has a plurality of reaction vessel pockets 301 which are arranged in the circumferential direction. The shaft 303 carrying the reaction table 302 and the shaft 313 carrying the sample table 315 and the reagent table 310 are driven by a driving system which will be described later in connection with another embodiment.

The system is also provided with a vibratory driving device (not shown) capable of vibrating the reaction table 302 at a high velocity and with a very small amplitude. This vibratory driving device also will be described in connection with another embodiment.

The reaction vessel pockets 301 receive reaction vessels 301'. In order to keep these reaction vessels 301' at a constant temperature, a thermostat cell 305 and a cold preserving cell 316 are provided as will be explained later.

A single pipetting device 317 is disposed between the reaction table 302 and the reagent table 310. The pipetting device 317 has an arm 300 which is pivotable about the axis of a shaft 304 and is movable up and down along the axis of the shaft 304. The arm 300 is provided at its free end with a probe 318 having a liquid removing and discharging function. Namely, the probe 318 is capable of removing samples from the sample vessels 314' in the sample vessel pockets 314 of the sample table 315 and discharging the same into the reaction vessels 301' in the reaction vessel pockets 301 of the reaction table 302. The probe 318 is also capable of sucking reagents from the reagent vessels 311 in the reagent vessel pockets 312a of the reagent table 310 and discharging the same into the reaction vessels 301' in the reaction vessel pockets 301 of the reaction table 302.

It will be understood that the pivotal support of the arm 300 enables the samples and the reagents to be transferred from the sample table 315 and the reagent table 310 to the reaction table 302 and the axial movement of the arm in the vertical direction enables the probe 318 to be moved to and from positions in the vicinity of the respective tables.

The reaction table 302 carries a fluorescent photometer 325 which is well known to those skilled in the art. The arrangement is such that a light emitted from a light source 326 is applied to successive reaction vessels 301' and the light transmitted through the reaction vessels is measured by the fluorescent photometer 325 or the light absorption photometer, thereby analyzing a sample such as antigen.

The reaction table 302 also carries a washing device 309 which will be described later in connection with another embodiment. The washing device 309 is movable towards and away from the reaction table 302 so as to wash the reaction vessels 301'. A second washing device 319 is provided between the reaction table 302 and the sample table 310 and is capable of washing the probe 318.

The operation and the manner of use of the analyzing system shown in FIG. 1 are as follows:

A sample which may be a liquid from a living body, such as antigen, blood serum, plasma or urine, is charged into the sample vessels 314' which are received in the sample vessel pockets 314. The reagent is selected in accordance with the purpose of the analysis. For instance, when immune reaction is to be examined, reagents composed of fine solids coated with antibody, a reaction-stopping reagent and a reagent for color reaction are used as the reagent. The reagent is changed in the reagent vessels 311 in the reagent pack pockets 312a of the reagent table 310.

The solid reagent may be of any form of solid which is constructed to react with the material to be measured, such as the vessel itself with the inner wall thereof coated with antibody, glass bead coated with antibody or fine particles coated with antibody.

As explained before, a plurality of packs 312 each including three reagent vessels 311 are arranged radially so that each pack can supply three different reagents. In the following description, however, an assumption is made for the purpose of simplification of explanation that two types of reagent; namely, a reagent composed of fine solid particles coated with antibody and a reagent for color reaction, are used in the analysis.

The arm 300 of the pipetting device 317 is swung so as to enable the probe 318 to remove a predetermined quantity of the sample from the sample vessel 314' in one of the sample vessel pockets 314 and to deliver the thus sucked sample into one of the reaction vessels 301' on the reaction table 302. After the discharge of the sample into the reaction vessel 301', the probe 318 of the pipetting device 317 is washed by the washing device 319 so as to prevent any contamination which may otherwise be caused by a carry-over of the sample. Subsequently, the reaction table 302 is vibrated for several seconds by the vibratory driving device and, thereafter, the reaction table 302 is rotated through an angle which corresponds to the pitch of arrangement of the reaction vessels. Meanwhile, the sample table 315 is also rotated to bring the next sample vessel to the pipetting position. This operation is repeated so that samples are successively transferred from the sample vessels 314' containing samples to be examined to a plurality of reaction vessels 301' on the reaction table 302.

Subsequently, the pipetting device 317 operates in a manner similar to that described above, so as to transfer reagents from the reagent vessels 311 to the successive reaction vessels 301' which have already been charged with the samples. More specifically, the transfer of the reagents is conducted from each reagent pack 312 such that the first reagent is removed and delivered first, the probe 318 is washed by the washing device 319 and then the second reagent is transferred. After the supply of the reagents, the reaction table 301 is vigorously vibrated again by the vibratory driving device so that the sample and the reagents are strongly stirred and mixed with each other. As a result, the antigen and the solid particles coated with antibody are caused to contact with each other with the result that the reactable portion of the antibody is bonded to the antigen. After the elapse of a time necessary for completion of the reaction, the solid reagents are washed away by the washing device 309 so that an unreacted portion of the mixture is discharged from the reaction vessels 301'. Subsequently, a framework which is an enzyme reaction liquid is added to the contents of the reaction vessels 301' by means of the pipetting device 317 thereby to cause coloring reaction. The probe 318 is washed by the washing device 319. After the completion of the coloring reactions in the reaction vessels, a light emitted from the light source 326 is caused to pass through the reaction vessels 301' and the transmitted light is measured by the fluorescent photo-meter, whereby the presence or absence of the antigen in each reaction vessel and the concentration thereof are analyzed.

Figure 2:
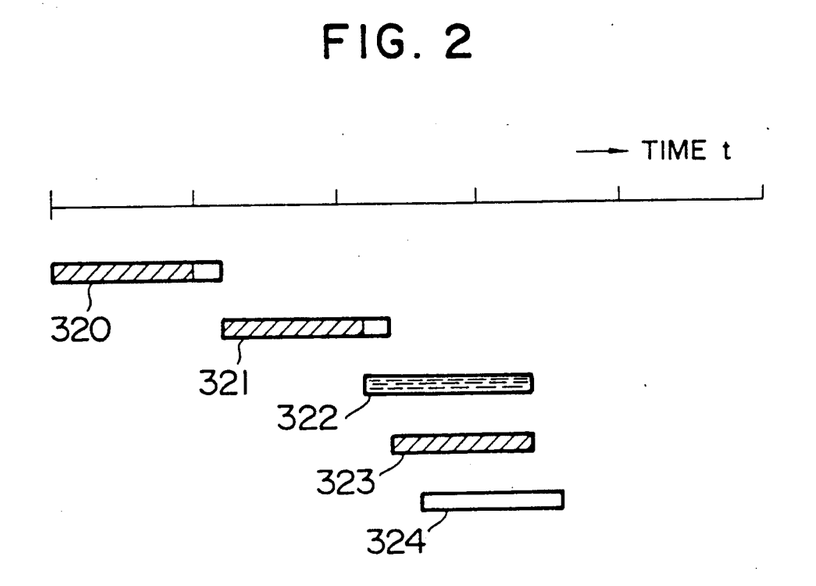
FIG. 2 shows a time chart of an analyzing process which is executed with the automatic analyzing system shown FIG. 1.

This operation will be explained in connection with FIG. 2 which is a time chart of the analyzing process. In this Figure, the axis t represents time. The hatched portion of a bar 320 represents the time required for the pipetting of the sample, while the blank portion of this bar 320 shows the time prepared for the washing of reaction vessels 301' by the washing device 309. No washing is conducted in this pipetting operation. The bar 321 shows the time required for the pipetting of the reagent. Similarly, bars 321, 323 and 324 show, respectively, the time lengths required for the steps of washing, coloring reaction reagent pipetting and photometry.

Another embodiment of the automatic analyzing system of the present invention will be described with reference to FIGS. 3 to 13. This embodiment is aimed at minimizing the size of the reagent cold preservation cell and providing a structure which is simple but yet capable of effectively shielding the interior of the reagent cold preservation cell from the ambient air.

Figure 4:
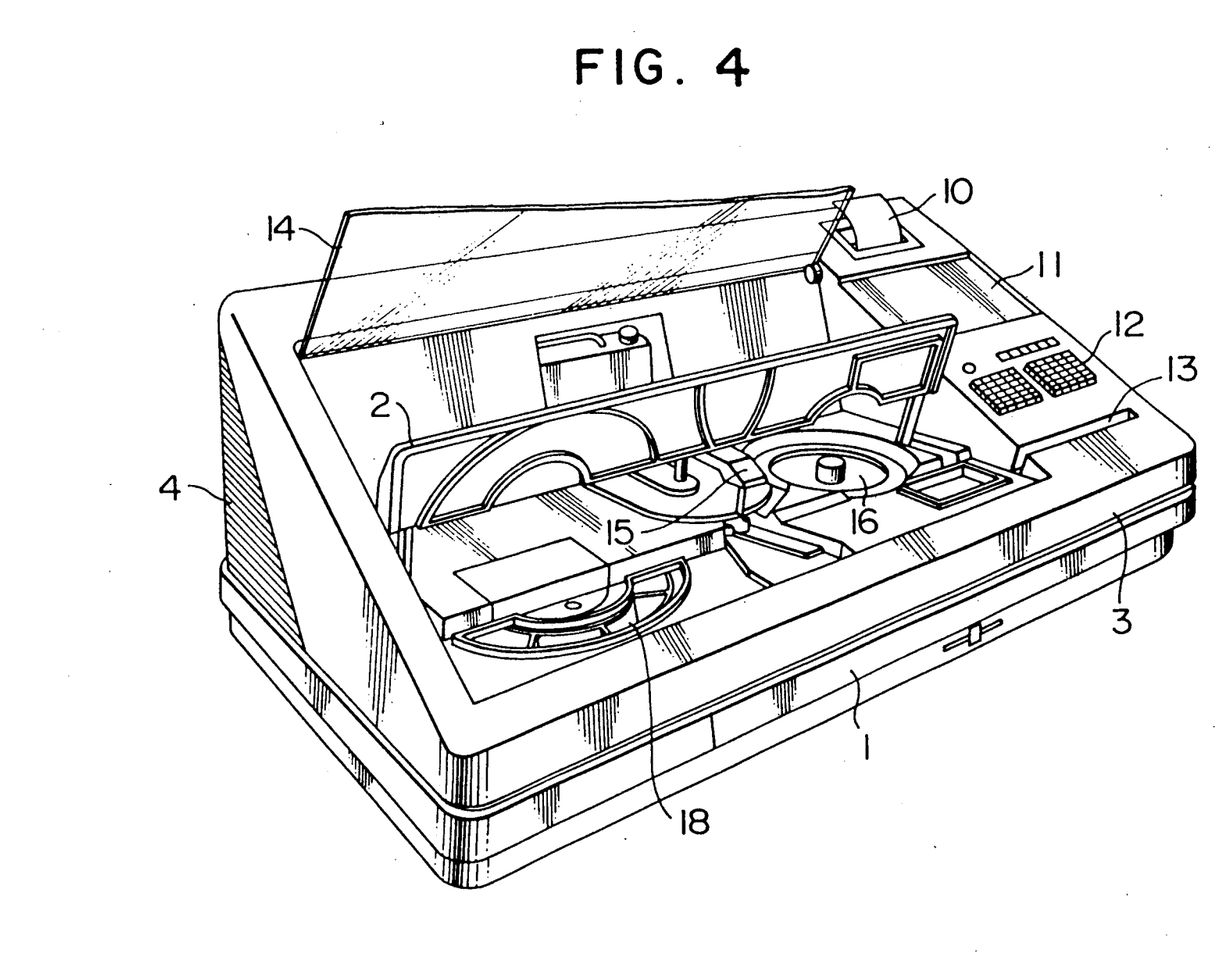
FIG. 4 is a perspective view of the embodiment shown in FIG. 3.
Figure 5:
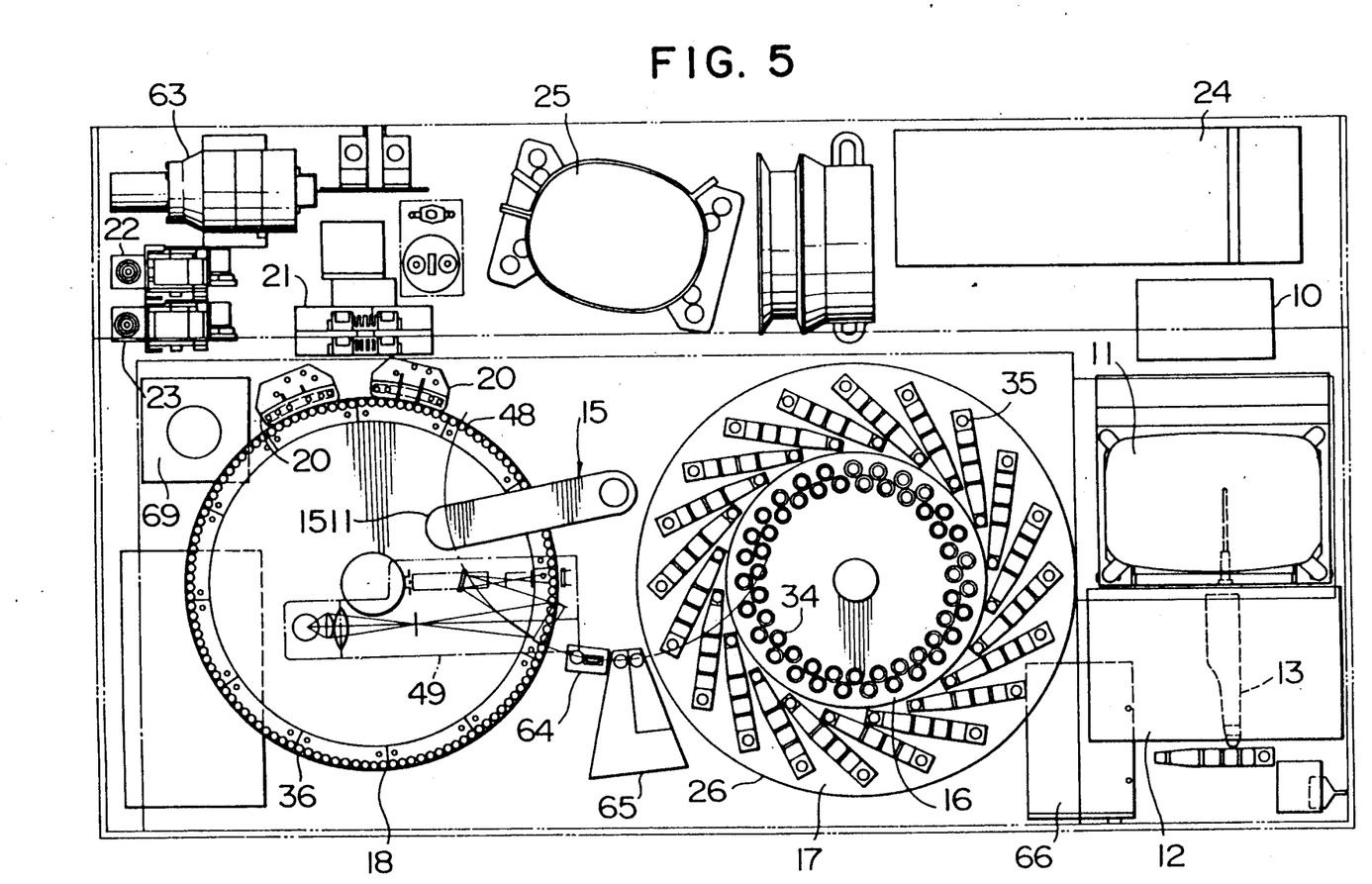
FIG. 5 is a plan view illustrating the arrangement of various units incorporated in the embodiment of FIG. 4.

FIG. 4 is a perspective view of the whole of this embodiment, while FIG. 5 is an illustration showing various units incorporated in this embodiment.

The automatic analyzing system shown in FIG. 4 has a base 1 which carries all the major units and wirings of the system. These units and wirings are covered by an intermediate cover 2 which is assembled with a frame 3. The system is enclosed by a left side cover 4, a right side cover and a rear cover. A printer 10, a CRT 11, a keyboard 12 and a bar code reader 13 are arranged on a right slanted surface of the frame 3 so as to be operated easily. The frame 3 has a large opening which is on the left side of the above-mentioned slanted surface as viewed in FIG. 4. This opening is normally closed by an upper cover 14 which is swingable between an open position and a close position. The upper cover 14 is made of a light-transmitting material so as to enable the user to observe the interior of the system. A pipetting device 15 and a sample table 16 are disposed under the above-mentioned intermediate cover 2 which is positioned below the upper cover 14. A reagent table 17 is disposed immediately below the sample table 16 coaxially therewith. The reagent table 17 is hidden behind the sample table 16 and, therefore, is invisible. A reaction table 18 on which the sample and the reagent are made to react is disposed at the left side of the stack of the sample table 16 and the reagent table 17. A washing device 20 capable of separating the reaction liquid from the solid reagents is secured to the underside of a slanted wall inside the upper cover 14 at a position adjacent to the reaction table 18.

A peristaltic pump 21 is disposed behind the washing device 20 and capable of sucking the reaction liquid through the washing device 20. A washing syringe pump 22 capable of supplying a washing liquid for washing the solid reagents and a pipetting syringe pump 23 for metering the samples and the reagents to be pipetted by the pipetting device 15 are provided on the inner side of the left side cover 4. A base plate unit 24 incorporating a microcomputer is disposed inside the right side cover, while a compressor unit 25 is disposed inside the rear cover. A plurality of reagent vessels 35 on the reagent table 17 are housed in a reagent cold preservation cell 26 which is cooled by chilled water to a temperature which is low enough to prevent degradation of the reagents. The cold preservation cell 26 is connected to a source of the chilled water. Any suitable cooling methods other that the cooling by chilled water, e.g., cooling by Peltier effect, may be used for maintaining the reagents at such a low temperature. The pipetting syringe pump 23 is connected by piping (not shown) to a probe tube of the pipetting device 15. A pump 63 disposed at a left rear portion of the system as viewed in FIG. 5 is capable of sucking water from a water tank 70 (see FIG. 12) and delivering the water for filling the pipetting syringe pump 23 and the pipetting device 15 up to the probe and for enabling the pipetting probe to conduct pipetting of the sample and the reagent, as well as for washing the probe.

The washing liquid in a washing liquid bottle 69 is used for washing the solid reagents after the discharge of the liquid from the reaction vessels 36. A fluorescent photometer 49 is disposed under the reaction table 18 so that the reaction vessels provided on the reaction table successively move across the path of light. Between two large tables 17 and 18 are disposed a washing tank 64 for washing the probe of the pipetting device 15 and a common reagent cell 65 which is used commonly for fluorescent photometry of different analysis items. The washing tank 64 and the common reagent cell 65 are disposed on a path of pivotal movement of the probe.

The reagent table 17 is housed in a reagent cold preserving cell 26 so as to be maintained at a temperature which is low enough to prevent degradation of reagents. A floppy disk drive (FDD) 66 is provided on the right lower side of the reagent cold preserving cell 26 and is capable of storing information concerning the conditions of analysis to be performed by the system. The construction of each unit of this system will be described hereunder.

Figure 3:
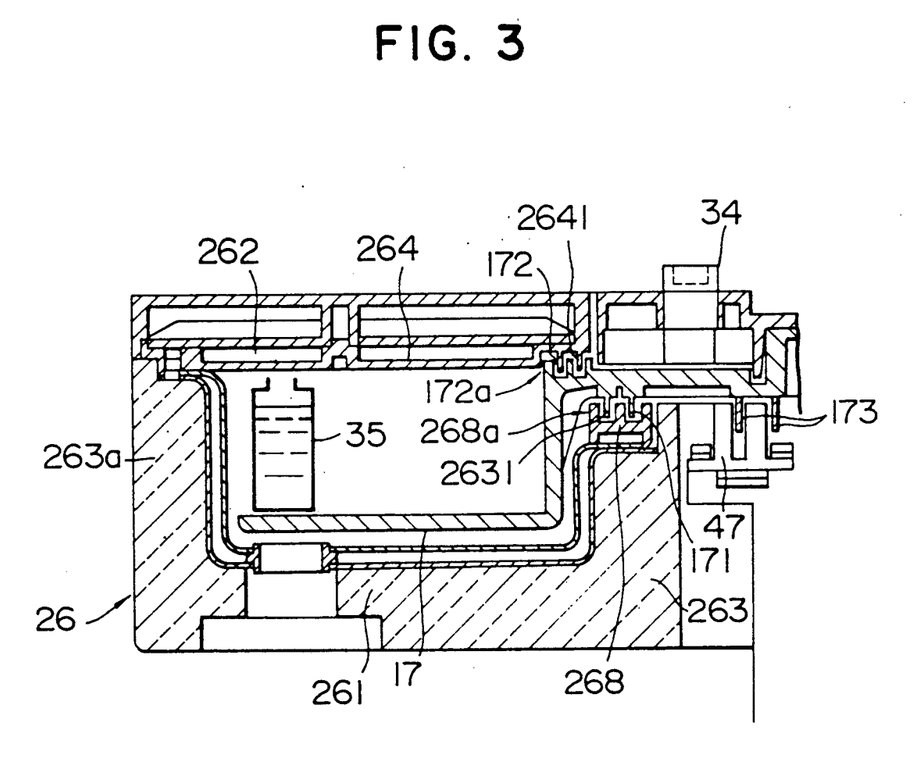
FIG. 3 is an enlarged fragmentary sectional view of a portion of another embodiment of the present invention.
Figure 6:
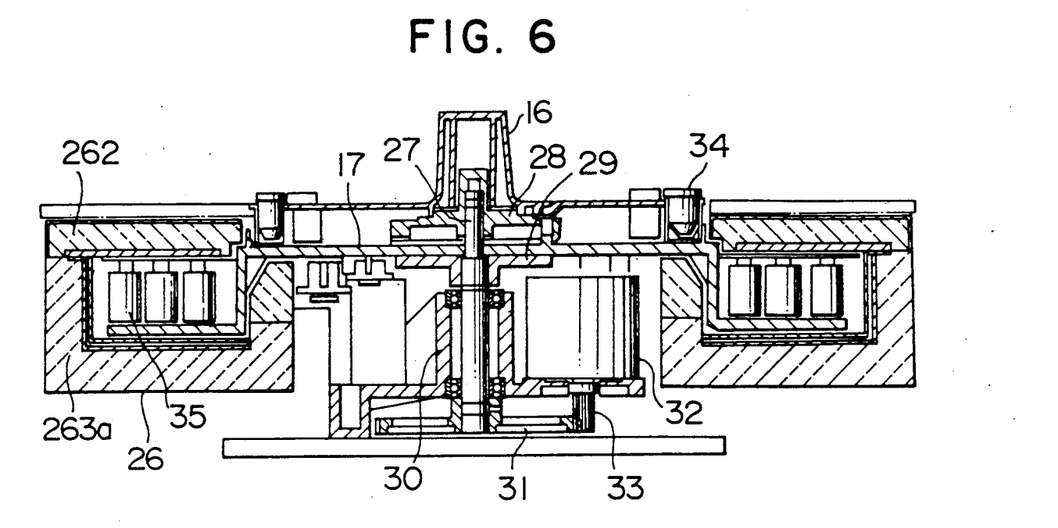
FIG. 6 is a sectional view of a sample table and a reagent table taken along the axis of rotation.
Figure 7:
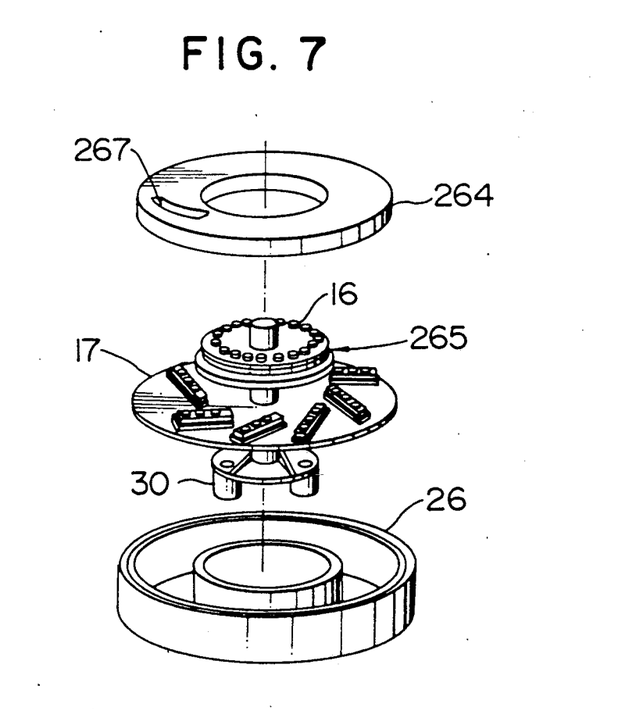
FIG. 7 is an exploded perspective view of the mechanism shown in FIG. 6.

FIG. 6 shows in section the sample table 16, the reagent table 17 and the reagent cold preserving cell 26, while FIG. 7 shows these parts in exploded perspective view. FIG. 3 is an enlarged sectional view of a portion of the arrangement shown in FIG. 6.

The sample table 16 is disposed above the reagent table 17 coaxially therewith. These tables 16 and 17 are secured to a common drive shaft 27 through brackets 28 and 29, respectively. The drive shaft 27 is rotatably supported by a bearing 30 and is provided at its lower end with a gear 31 which engages with a pinion 33 fixed to the output shaft of a pulse motor 32. The sample table 16 carries a plurality of sample vessels 34 which are arranged along the outer peripheral edge of the table 16. Similarly, a plurality of reagent vessels 35 are arranged along the outer peripheral edge of the reagent table 17. The reagent table is housed together with the reagent vessels 35 in the reagent cold preserving cell 26. The cold preserving cell 26 has an annular form and is arranged such that the portion of the reagent table 17 near the outer peripheral edge of the table 17 moves in the cold preserving cell 26 as the reagent table 17 is rotationally driven by the drive shaft 27 which is rotated by the power of the pulse motor 32. The reagent cold preserving cell 26 has lower, upper, radially inner and outer heat-insulating walls 261, 262, 263 and 263a which cooperate together to define an annular space. The reagent cold preserving cell 26 is also provided with a cold preserving cell cover 264 which closes the above-mentioned annular space. A disk section 265 (see FIG. 7) including the sample table 16 and the reagent table 17 are secured to the drive shaft 27 together with the bearing 30. The cold preserving cell cover 264 is provided with a probe insertion port 267 for enabling the probe of the pipetting device 15 to be inserted into the cell 26.

Referring to FIG. 6, a seal means is provided between the cold preserving cell 26 and the reagent table 17. The detail of the seal will be described with specific reference to FIG. 3. A pair of annular grooves 2631 are provided in the upper end of the inner wall 263 of the reagent cold preserving cell 26. A pair of annular ribs 171 formed on a portion of the lower surface of the reagent table 17 opposing these grooves 2631 are received in these annular grooves so as to form a labyrinth seal 268a. A similar labyrinth seal 172a is formed also between the upper surface of the reagent table 17 and the reagent cold preserving cell cover 264. More specifically, the latter labyrinth seal 172a includes a pair of annular ribs 2641 formed on the lower surface of the reagent cold preserving cell cover 264 while mating annular grooves 172 are formed in the upper surface of the reagent table 17 facing the reagent cold preserving cell cover 264. These ribs 171 and 2641 and the corresponding grooves 2631 and 172 are slightly spaced apart from each other so that they do not directly contact each other. The labyrinth type seals 268a and 172a provided between the rotatable reagent table 17 and the stationary reagent cold preserving cell 26 provides the following effect: Namely, when the analyzing system is started, chilled air flows through the minute gaps between the grooves 2631 and 172 and the corresponding ribs 171 and 2641 so that the chilled air forms dew due to difference in the temperature between the chilled air and the ambient air. The dew forms droplets which are accumulated in the grooves 2631 and 172 and grow to such an extent as to clog the minute gaps between the grooves and the ribs, thus preventing further leakage of the chilled air. The dewing is ceased accordingly.

A detection plate 173 is secured to the lower side of a part of the reagent table 17 which is radially inwardly of the seal 268a. This detection plate 173 cooperates with a photo-interrupter 47 to detect a state of interruption of a light so that the rotation of the reagent table 17 is controlled by a controller (not shown) in accordance with the result of the detection.

The multiplicity of sample vessels 34, which are arranged in two rows along the outer peripheral edge of the sample table 16, and the multiplicity of reagent vessels 35 arranged on the reagent table 17 are arranged around the axis of the common drive shaft 27 such that the vessels 34 and 35 do not radially overlap each other. Although the pipetting device 15 has only one probe 1513 (see FIG. 8), the above-described arrangement of the sample vessels and the reagent vessels enables the single probe of the pipetting device 15 to suck the samples and the reagents on the path of movement thereof and transfer them to the reaction vessels on the reaction table 18.

Figure 11:
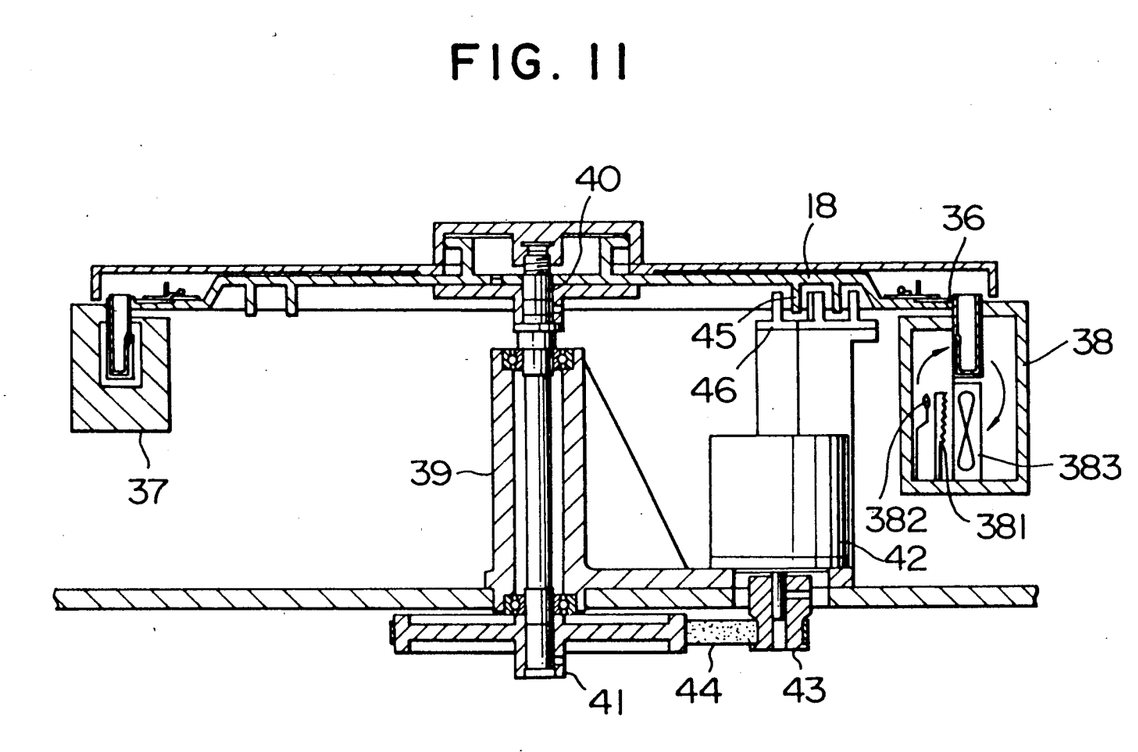
FIG. 11 is a sectional view of a reaction table taken along the axis thereof.

The construction of the reaction table 18 will be described in detail with reference to FIG. 11.

The reaction liquid in the reaction vessels 36 arranged along the outer periphery of the reaction table 18 is held at a constant temperature, for example, 37° C. within an annular air thermostat tank 37 to assure a stable reaction. The thermostat tank 37 is provided with an air circulation chamber 38 through which heated air is circulated so as to heat the reaction liquid up to 37° C. in a short time. The air circulation chamber 38 has a heater 381 for heating the air to maintain the air temperature at 37° C., a temperature sensor 382 and a blower 383. The reaction table 18 is fixed to the upper end of a drive shaft 40 which is rotatably supported by a driving base 39. The drive shaft 40 is provided at its lower end with a pulley 41 which is drivingly connected through a timing belt 44 to a pulley 43 on a pulse motor 42. The angle of rotation of the reaction table 18 is detectable by means of a detection plate 45 which is formed integrally with the reaction table 18 and which cooperates with a photo-interrupter 46 to detect the state of interruption of a light.

Figure 8:
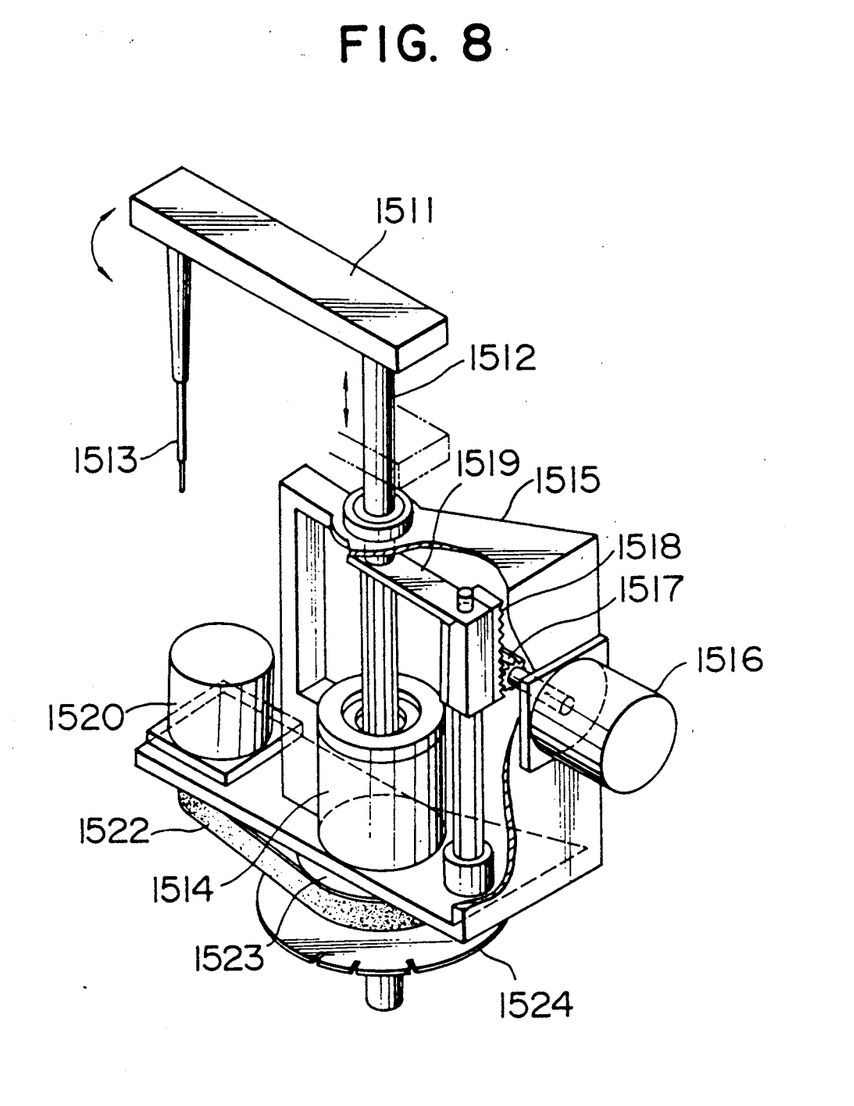
FIG. 8 is a perspective view of a pipetting mechanism.

FIG. 8 shows the construction of the pipetting device 15. The pipetting device 15 has a pipetting arm 1511 which is fixed at its one end to a drive shaft 1512 while the other end carries a single probe 1513 secured thereto. The drive shaft 1512 is supported by a ball spline bearing 1514 so as to be movable up and down and is rotatably supported by a frame 1515. The vertical movement of the drive shaft 1512 is effected by the power of a pulse motor 1516 transmitted through a pinion 1517, a rack 1518 and a vertically movable frame 1519. The rotation of the drive shaft 1512 is effected by another pulse motor 1520 the output of which is transmitted to the ball spline bearing 1514 through a pulley (not shown) on the lower side of the output shaft of this pulse motor 1520, a timing belt 1522 and a pulley 1523.

The arrivals of the pipetting arm 1511 at the upper and lower ends of its stroke are detected by a combination of a detection plate (not shown) and a photo-interrupter (not shown), while the detection of angular position of the arm is conducted by a detection plate 1524 which cooperates with another photo-interrupter which is not shown. Thus, the vertical position and the rotational position of the pipetting arm are controlled by a controller which receives signals from these detection plates. The probe 1513 is rotatable to cover an area between the inner row of the sample vessels 34 arranged on the sample table 16 shown in FIG. 5 and the sample discharge port 48 through which the sample is discharged into the reaction vessels 36 arranged on the reaction table 18.

The samples and the reagents supplied into the reaction vessels 36 by the pipetting device 15 are heated to the afore-mentioned constant temperature which is 37° C. for example so as to react with each other. After the elapse of a predetermined reaction time, a washing operation is performed by a washing device 20 which is disposed adjacent to the reaction table 18 in order to wash the reaction liquid away from the reaction vessels 36. For instance, in case of the measurement of an immune reaction, a solid phase and a liquid phase generated as a result of the antigen/antibody reaction are separated by the washing operation.

Figure 9:
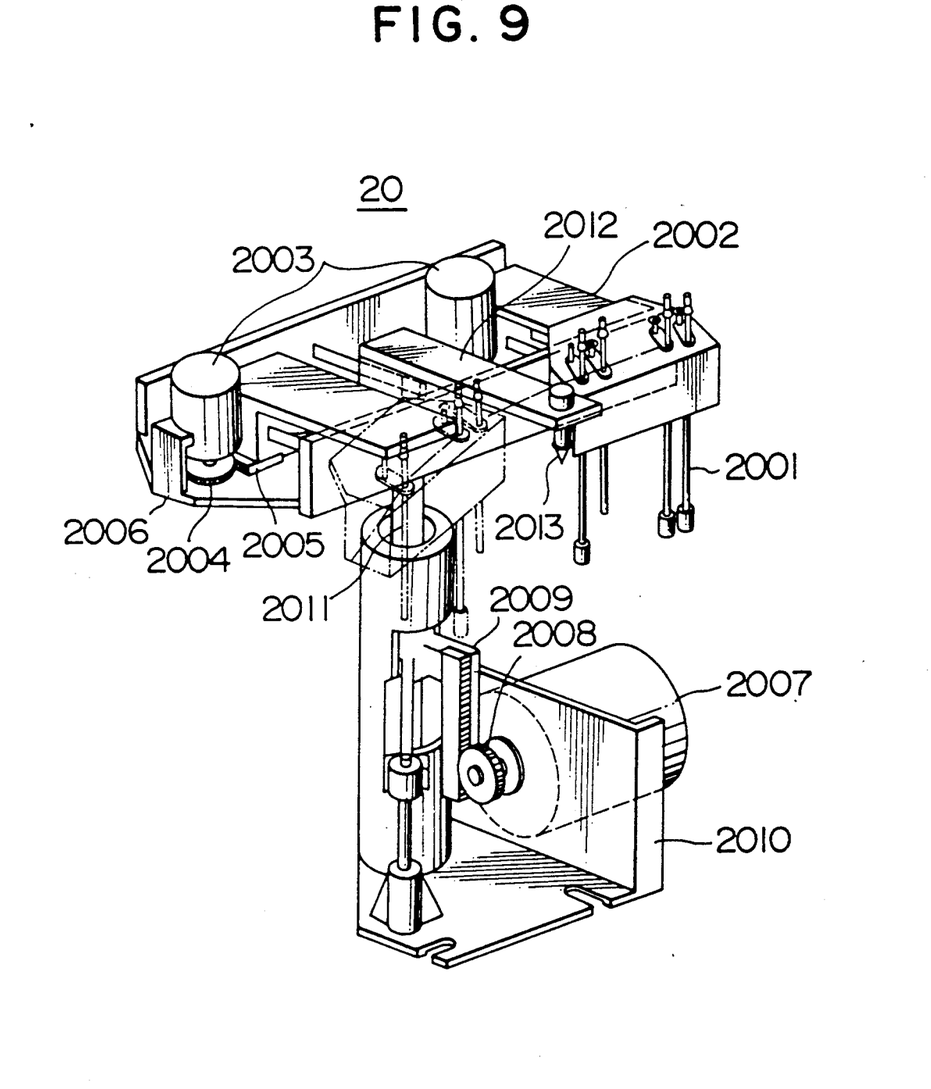
FIG. 9 is a perspective view of a washing unit.

FIG. 9 shows the details of the washing device 20. The washing device 20 has washing nozzles 2001 secured to a washing arm 2002. The washing arm 2002 is provided with a rack 2005 engaging with a pinion 2004 fixed to the output shaft of each of a pair of drive motors 2003 so that the washing arm 2002 is movable back and forth by the force of the motor 2003. The forward-/backward driving unit is secured to a vertically movable frame 2006 and is adapted to be moved up and down together with the frame 2006 by a drive shaft 2011 carried by a base 2010, and vertically movable by the a cooperation between a pinion 2008 on the output shaft of a pulse motor 2007 and a rack 2009. A membrane breaking mechanism 2012 is secured to the frame 2006. The membrane breaking mechanism 2012 has a membrane breaking bar 2013 which is movable vertically so as to break a membrane (not shown) closing the opening of each reaction vessel 36 for the purpose of preventing evaporation of the reaction liquid or for other purposes such as prevention of jumping out of stirring balls or tablets charged in reaction vessels 36.

After the separation of the liquid phase and the solid phase in each reaction vessel 36, the liquid phase is discharged by means of the washing nozzle 2001. Then, a reagent which enables the remaining solid phase to produce fluorescent luminance is delivered into the reaction vessels by means of the pipetting device 15. After the elapse of a predetermined time, the intensity of fluorescent luminance is measured by the fluorescent photometer 49.

Figure 10:
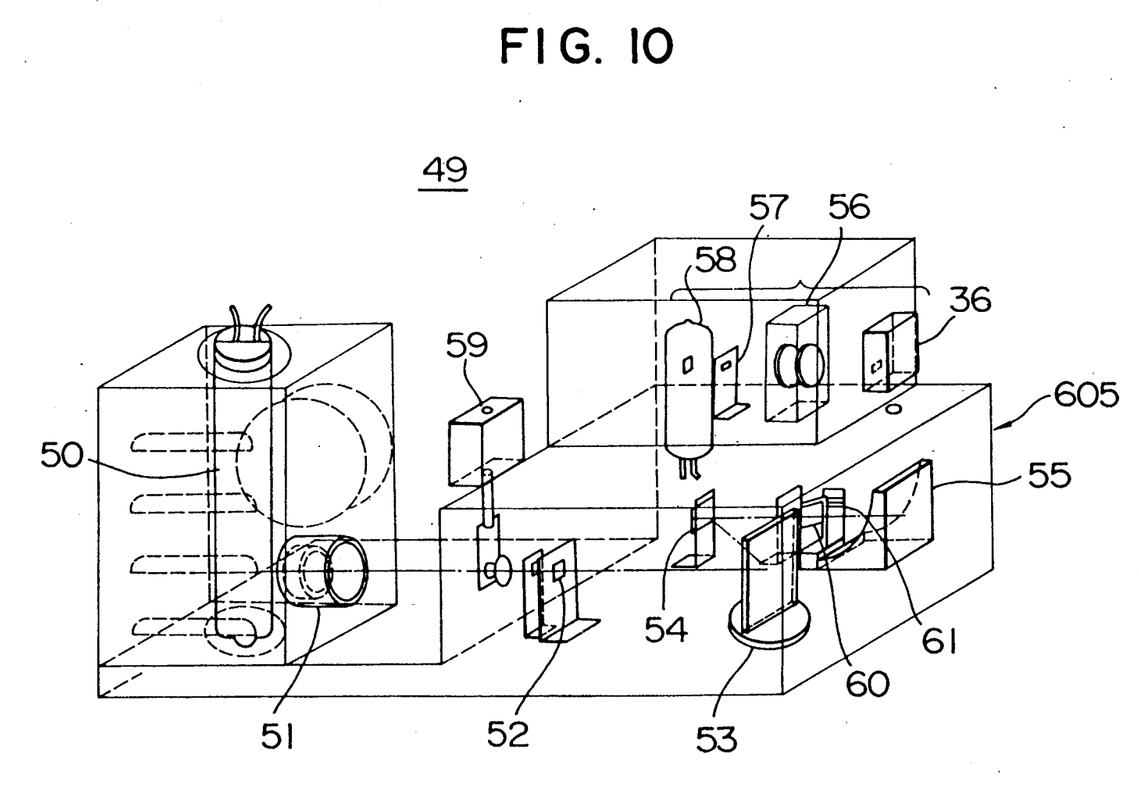
FIG. 10 is a schematic illustration of an optical system in a fluorescent photometer.

FIG. 10 illustrates the construction of the fluorescent photometer 49. The light emitted from a light source lamp 50 is condensed by the lens 51 and is contracted through a mask 52. Then, the light of the required excitation wavelength is picked up through a grating 53 in a spectrometer 605 of the excitation side of the photometer. The light of the excitation wavelength is reflected by a mirror 54 so as to impinge upon a troidal mirror 55 which collects the scattered light so as to focus the light on a predetermined portion in the reaction vessel 36. When the light of the excitation wavelength is applied to the reaction liquid in the reaction chamber, the light of fluorescent wavelength of an intensity proportional to the density of the reaction liquid is produced from the entire circumference of the liquid. The fluorescent photometer 49 used in the embodiment of the present invention is designed to detect the fluoroescent wavelength light which is perpendicular to the direction of the incidence of the excitation wavelength light. The detected fluorescent light is condensed through a lens 56 and is made to pass through a wavelength-selection filter and mask 57 so as to impinge upon a photo-multiplier tube 58, whereby an electric signal of a level proportional to the fluorescent light intensity is produced by the photo-multiplier tube 58. In order to automatically compensate for the drift of the fluorescent photometer, the level of dark current in the photo-multiplier tube 58 is measured by making use of a shutter 59. At the same time, a light split by a half mirror 60 is received by a photo-diode 61. The output level of the source lamp 50 is monitored and controlled in accordance with the output from the photo-diode 61.

Figure 12:
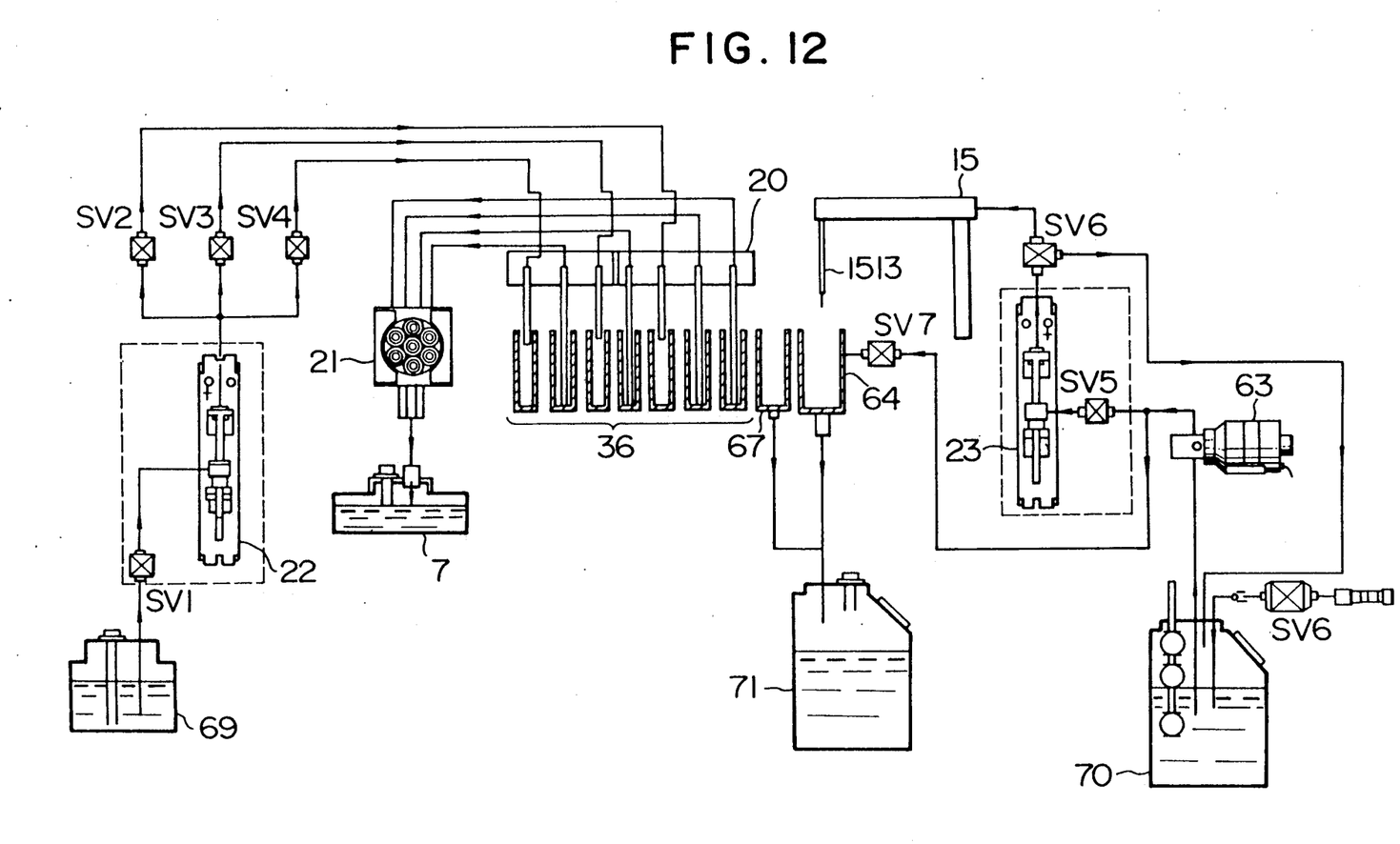
FIG. 12 is a schematic illustration of liquid lines.
Figure 13:
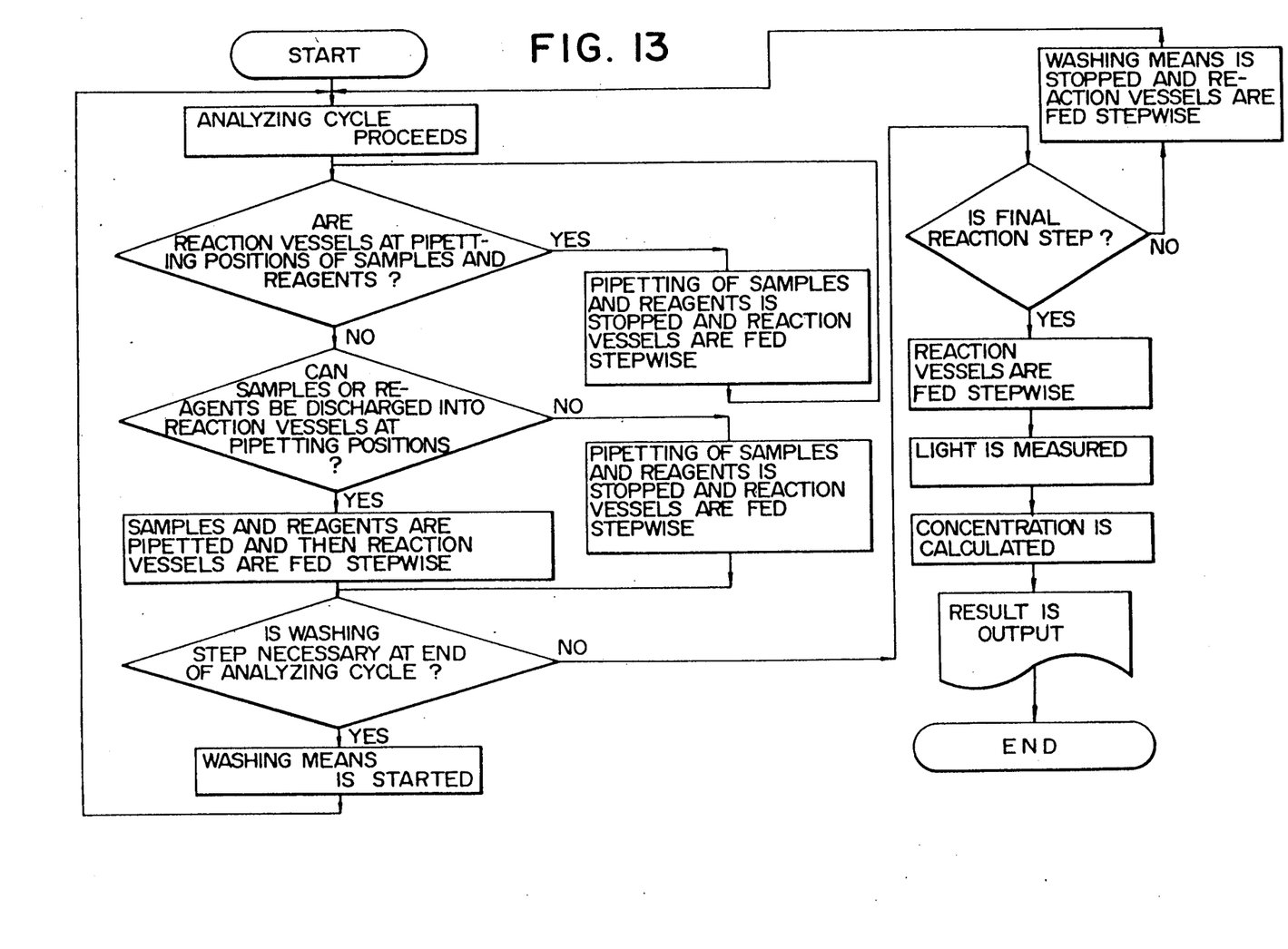
FIG. 13 is a flow chart explanatory of the analyzing process executed with the automatic analyzing system of the present invention.

FIG. 12 shows various liquid lines arranged in the embodiment shown in FIG. 4. These lines are broadly classified into four systems. A first liquid line system extends from a water tank 70 containing ionized water or distilled water to the probe 1513 of the pipetting device 15 through the pump 63 for sucking the water from the tank 70 and then through the pipetting syringe pump 23. A second liquid line system includes a drain pipe from a washing tank 64 for washing the probe and for receiving liquid discharged from the probe, as well as a drain pipe from an air purge tank 67 for discharging the washing liquid from the washing bottle 69 during air-purging of the washing device 20. These drain pipes are connected into a common pipe which leads to a drain tank 71. A third liquid line system includes lines through which a washing liquid is sucked from the washing bottle 69 by a washing syringe pump 22 and discharged to the reaction vessels 36 by means of the washing nozzle 2001 of the washing device 20. A fourth liquid line system includes lines for sucking up the reaction liquid from the reaction vessels 36 by the perista pump 21 through another washing nozzle 2001 of the washing device 20 and for discharging the sucked reaction liquid into a waste liquid bottle 7. In FIG. 12, symbols SV1 to SV7 show stop valves. The operation of this embodiment will be described hereinunder.

Necessary analyzing conditions are input in a dialogue manner by means of the CRT 11 and the keyboard 12. Then, reagent vessels 35 are set on the reagent table 17 after reading the bar codes on the reagent vessels 35 by means of the bar code reader 13. A plurality of reagent vessels 35 are arranged on the reagent table 17 in accordance with the items of analytical measurement, as shown in FIG. 5. On the other hand, sample vessels 34 charged with the samples to be analyzed are set on the sample table 16. In addition, reaction vessels 36 for receiving the samples and the reagents are arranged over the entire circumference of the reaction table 18. The common reagent bottle 65 and the washing liquid bottle 69 are also set on predetermined portions of the analyzing system. Information concerning the analyzing conditions including the types of reagents and samples and so forth is printed by means of the printer 10. The analyzing system is now ready to operate. As a start switch on the keyboard 12 is turned on, an operation is commended for checking conditions such as the state of setting of the reaction vessel 36, the amount of the common reagent in the common reagent bottle 65 and the amount of washing liquid in the washing bottle 69. At the same time, the pump 63 is operated to effect air-purge of the liquid line system. The checking operation is automatically performed as an initial routine for initializing the whole system. In case of any abnormality in the result of the check, an alarming buzzer goes off to inform the operator of the occurrence of the abnormality. In addition, the state of the abnormality is displayed on the CRT 11 and the data concerning the abnormality is printed out by the printer 10. The process proceeds to a next step when no abnormality is found through the checking operation. The analyzing cyclic operation is then started. The analyzing process will be described with reference to a flow chart shown in FIG. 13.

Liquids extracted from living bodies, such as a liquid containing antigen, blood serum, plasma and urin are usable as the samples. The reagents used in this system are those used ordinarily. In case of an analysis of immune reaction of fine virus, a solid reagent coated with antibody is suitably used. The sample vessels 34 are heated up to and maintained at the predetermined temperature in the reagent thermostat cell. The sample exhibits a large fluctuation in the viscosity between 1 and 8 cps at room temperature. The characteristics of the samples will be lost if the samples are heated to a to high temperature. On the other hand, a too low temperature of the samples will increase the viscosity to such an extent as to impair the accuracy of metering performed by the probe 1513 of the pipetting device 15. It is therefore necessary that the samples are heated to and maintained at a temperature which is slightly lower than the normal temperature. On the other hand, the reagent vessels 35 are held in the reagent cold preserving cell 26 so as to be maintained at a predetermined temperature, e.g , 8° C., which is suitable for shelving the reagents stably for a long period.

A predetermined quantity of the sample is sucked up from the sample vessel 34 on the sample table 16 by means of the probe 1513 of the pipetting device 15 and is transferred to and discharged into a designated reaction vessel 36 on the reaction table 18. After the discharge of the sample, the probe 1513 of the pipetting device 15 is well washed in the washing tank 64 to eliminate any contamination which may otherwise be caused by a carry-over of the sample. Subsequently, the reaction table 18 is vibrated for several seconds by the vibratory driving device which is composed of the pulse motor 42, the pulley 43, the timing belt 44, the pulley 44 and the drive shaft 40, thereby shaking and stirring the reaction liquid. Then, the reaction table 18 is rotated by an amount which corresponds to the pitch of arrangement of the reaction vessels. Meanwhile, the sample table 16 is rotated to bring a succeeding sample vessel 34 to the sucking position. This operation is repeated until all the necessary reaction vessels 36 are charged with the samples. Then, a similar cyclic pipetting operation is executed to suck the reagents from the successive reagent vessels 35 and to discharge the same into the respective reaction vessels 36. When a plurality of types of reagents are used, the transfer of the first reagent is followed by the transfer of the second reagent. The reaction table 18 is thus rotated in an indexed manner so as to transfer the samples and reagents into the successive reaction vessels 36 on the reaction table 18. It will be seen that the construction of the analyzing system is simplified due to the use of the described pipetting system. The described mode of pipetting, however, is not exclusive. For instance, the pipetting and the rotation of the reaction table 18 may be executed in such a manner that, after delivering a sample into a reaction vessel 36 by means of the pipetting mechanism 15, the probe of the pipetting mechanism is washed and then used for pipetting the reagent into the same reaction vessel 36 while the reaction table 18 is kept stationary. Thus, the reaction table 18 may be rotated intermittently after filling each reaction vessel both with the sample and the reagent. Form the view point of simplification of the construction and operation of the analyzing system, however, the first-mentioned mode of pipetting operation, i.e., delivery of the reagent to successive reaction vessels 36 after charging of these reaction vessels with samples, is preferred.

The reaction between the samples and a reagent will be described with specific reference to the case of a high-sensitivity immune measurement, though the nature of the reaction performed in the analyzing system of this embodiment has already been described briefly. A reagent used is composed of a solid coated with antibody. Samples containing antigen such as virus are charged into the reaction vessels and the above-mentioned reagent composed of solid coated with antibody is added to the samples. The reaction table carrying the reaction vessels 36 is then vigorously vibrated by the vibratory driving device which includes the pulse motor 42 controlled in accordance with a driving control signal, whereby the sample and the reagent in each reaction vessel are strongly stirred and blended. Consequently, the antigen and the solid carrying the antibody contact with each other so that the reactable portion of the antibody is boded to the antigen. After the elapse of a predetermined time necessary for the reaction, the solid reagent is washed and unreacted liquid which causes noises in the high-sensitivity measurement is discharged by means of the nozzle of the washing device 20. Then, the solid reagent is washed again by the washing liquid supplied from another nozzle of the washing device. The washing device 20 can be moved up and down as required. After washing the solid reagent, a framework which is an enzyme reaction liquid is added to cause coloring reaction. Then, the light from the source lamp 50 is applied to the reaction vessel 36 and the fluorescent luminance from the content of the reaction vessel is measured by the fluorescent photometer 49, thereby analyzing antigen. Obviously, the analyzing system described hereinbefore can also be used for ordinary antigen/antibody reaction, though a high-sensitivity measurement of immune reaction has been specifically mentioned.

The ability of conducting the high-sensitivity measurement of immune reaction enables this system to be used for diagnosis of acquired immune deficiency (AIDS). The described system can perform a highly accurate measurement of antigen in the sample on the order of $10^{-6}$ to $10^{-13}$ Mol/l in terms of the antigen content. It is to be noted that all the known biochemical analyzing systems could provide only a low level of sensitivity, e.g., $10^{-6}$ Mol/l or less. Thus, the analyzing system of the invention provides a sensitivity which is about $10^6$ times as high as that of known analyzing systems.

The operation of the portions of the apparatus around the reagent table 17 will be described in detail with reference to FIG. 3. Though the arrangement has already been described, the parts and components around the reagent table 17 will be described again for the purpose of facilitating the understanding of operation.

The portion of the reagent table 17 carrying the reagent vessels 35 is housed in the reagent cold preserving cell 26. In order to allow the reagent table 26 to rotate relative to the reagent cold preserving cell 26 which is stationary, it is necessary that minute gaps be left between the table 17 and the cell 26 at both sides of the table 17. In operation, therefore, the chilled air escapes from the reagent cold preserving cell 26 through these gaps and the chilled air leaking through these gaps tends to form dew upon contact with the ambient air due to difference in the temperature and humidity between itself and the ambient air. The dew progressively grows and forms a water pool, with the result that the chilled air is wastefully consumed. In consequence, the compressor of the refrigeration system for cooling the air is required to have a large capacity and consumes much energy.

It would be possible to seal the gaps between the reagent table 17 and the reagent cold preserving cell 26 by means of low-friction and anti-wear packings. Such packings, however, are still unsatisfactory in that the packings are worn sooner or later and the load torque is increased due to friction however the friction and the wear of the packing material may be small.

In order to overcome this problem, the described embodiment employs seals 172a and 268a of the type described before with reference to FIG. 3. In the initial period of operation of the analyzing system, the chilled air escapes from the reagent cold preserving cell 26 through the labyrinth type seals 172a and 268a. The flow rate of the escaping chilled air, however, is limited because of the labyrinth-type structure of the seal so that a large sealing effect is obtained as compared with the straight gaps. When any temperature and moisture differences exist between the chilled air and the ambient air, the dew generated in the labyrinth type seals grows into dew droplets which then gather to fill the grooves of the labyrinth type seals. In consequence, the gap between the groove 2631 and the rib 171 and the gap between the groove 172 and the rib 2641 is completely filled with the water so that the escape of the chilled air does not take place any more. In consequence, the reagent table can smoothly rotate without substantial resistance while maintaining effective seal between itself and the reagent cold preserving cell.

As will be understood from the foregoing description, the automatic analyzing system of the present invention has a plurality of reagent packs arranged on the reagent table, each pack including a plurality of reagent vessels containing different reagents corresponding to different analytical measurement items. These packs are replaceable in accordance with a change in the analytical measurement item or items. In addition, the reagent table and the sample table are driven by a common drive system and the samples and reagents are transferred to the reaction vessels by means of a single pipetting device. In consequence, the pipetting arrangement and the driving arrangement are remarkably simplified. Thus, the analyzing system of the present invention can be realized in the form of a compact desk-top type device. It is also to be understood that the analyzing system of the present invention is suitable for use in the cases where a multiplicity of types of reagent are employed for each analytical measurement item, as in the case of the current immune reaction measurement which generally use up to 5 types of reagents. In addition, the analyzing system of the present invention, which is easy to operate, can be used in various types of biochemical analysis including clinical analysis.

In particular, the labyrinth type seal provided between the rotatable reagent table and the stationary reagent cold preserving cell effectively prevents the chilled air from escaping from the reagent cold preserving cell without frictional resistance. This seal is highly reliable because of its simple construction and contributes to saving energy because the wasteful consumption of chilled air is minimized.

In generally, automatic analyzing system of the type of which the invention pertains suffers from a disadvantage that the liquid lines formed by flexible tubes are arranged in quite a complicated manner so that the tubes tend to be entangled with each other to allow stagnation of liquids in bent or recessing portion of these tubes, with the result that various kinds of bacteria are allowed to glow so as to clog these tubes. This problem, however, is overcome by the analyzing system of the present invention because the liquid lines or channels in the system of the present invention can be formed of rigid or hard tubes such as hard vinylchloride tubes which can be arranged at suitable degrees of inclination so as to promote natural flow of the liquids.

What is claimed is:

1. An automatic analyzing system comprising:
a rotatable sample table for supporting a plurality of sample vessels;
a rotatable reagent table disposed coaxially with said sample table and including a substantially annular portion adjacent an outer peripheral edge of said reagent table, said annular portion being designed to support a plurality of reagent vessels arranged thereon in a substantially annular row;
a shaft commonly provided for said sample and reagent tables;
a rotatable reaction table disposed in a side-by-side laterally spaced relationship to said sample and reagent tables and adapted to support a plurality of reaction vessels;
a single pipetting device including a probe movable between said sample table and said reaction table and between said reagent table and said reaction table to remove samples and reagents from selected sample vessels on said sample table and from selected reagent vessels on said reagent table and deliver the samples and reagents to selected reaction vessels on said reaction table;
an annular stationary reagent cold preserving cell capable of housing the annular row of said reagent vessels on said annular portion of said reagent table to keep the reagents in said annular row of reagent vessels at a temperature low enough to prevent degradation of the reagents;
said cold preserving cell including lower, upper, radially inner and outer heat-insulating walls cooperating together to define a substantially annular space accommodating said annular portion of said reagent table and the annular row of reagent vessels thereon such that said annular portion and said annular row of reagent vessels are movable together circumferentially of said reagent table, said radially inner and upper heat-insulating walls respectively having lower and upper surfaces spaced axially of said reagent table to allow said annular portion of said reagent table to extend radially outwardly into said annular space;

said lower and upper surfaces of said reagent table being spaced from upper and lower surfaces of said radially inner and upper heat-insulating walls to cooperate therewith to define first and second gaps; and at least one annular labyrinth seal provided in one of said first and second gaps.

2. An automatic analyzing system according to claim 1, wherein said sample table is provided with sample vessel pockets disposed radially inwardly of said reagent cold preserving cell.

3. An automatic analyzing system according to claim 1, wherein an annular labyrinth seal is provided in each of said first and second gaps, and each of said labyrinth seals is formed by at least one annular groove and at least one annular disposed in closely spaced relationship, said annular groove being provided on one of said reagent table and said cold preserving cell and said annular rib being provided on the other of said reagent table and said cold preserving cell.

* * * * *